United States Patent [19]

Hayashi

[11] 4,079,080

[45] Mar. 14, 1978

[54] PREPARATION OF KETAZINE AND CATALYST THEREFOR

[75] Inventor: Hiromu Hayashi, Tokushima, Japan

[73] Assignee: Sumitomo Chemical Company, Limited, Osaka, Japan

[21] Appl. No.: 787,724

[22] Filed: Apr. 15, 1977

[30] Foreign Application Priority Data

Apr. 15, 1976 Japan .................................. 51-43450

[51] Int. Cl.² ............................................. C07C 119/00
[52] U.S. Cl. ............................. 260/566 B; 252/429 R; 252/431 N
[58] Field of Search ............... 260/566 B; 252/429 R, 252/431 N

[56] References Cited

U.S. PATENT DOCUMENTS

| | | | |
|---|---|---|---|
| 2,870,206 | 1/1959 | Meyer et al. | 260/566 B |
| 3,793,359 | 2/1974 | Stapfer et al. | 260/431 N X |
| 3,966,782 | 6/1976 | Cipriani et al. | 260/431 N X |

*Primary Examiner*—Gerald A. Schwartz
*Attorney, Agent, or Firm*—Sughrue, Rothwell, Mion, Zinn and Macpeak

[57] ABSTRACT

A process for the preparation of a ketazine, such as benzophenone azine, comprising oxidizing a ketimine with molecular oxygen in the presence of a high molecular weight catalyst prepared by coordinating a copper (I) halide or a methoxy copper (II) halide, if desired, together with a third component, to a synthetic resin containing therein monodentate pyridine groups as functional groups, such as poly(2- or 4-vinylpyridine), the catalyst used therein and a method for preparing the catalyst.

5 Claims, No Drawings

PREPARATION OF KETAZINE AND CATALYST THEREFOR

BACKGROUND OF THE INVENTION

1. Field of the Invention

The present invention relates to a high molecular weight catalyst for producing ketazines, a method for producing the high molecular weight catalyst and a method for producing ketazines comprising reacting ketimines with molecular oxygen using the catalyst.

2. Description of the Prior Art

Ketazines are generally produced by reacting ketones and hydrazine. The drawback of this process is the use of expensive hydrazine. The present invention relates to a method for producing ketazines, such as benzophenone azine, $(C_6H_5)_2C=N-N=C(C_6H_5)_2$, by oxidation of ketimines, such as diphenylmethane imine, $(C_6H_5)_2C=NH$, without using such hydrazine.

A ketimine, e.g., diphenylmethane imine, is easily produced by the gas-phase reaction of benzophenone $[(C_6H_5)_2C=O]$ and ammonia $(NH_3)$ in the presence of thoria $(ThO_2)$ or thoria-silica $(ThO_2\text{-}SiO_2)$, or by the liquid-phase reaction of benzophenone and ammonia, at atmospheric pressure or under an ammonia pressure, in the presence of zinc chloride $(ZnCl_2)$ or ammonium chloride $(NH_4Cl)$. A method for producing benzophenone azine from diphenylmethane imine and molecular oxygen in the presence of copper (I) chloride, CuCl, is disclosed in U.S. Pat. No. 2,870,206. Another method for producing benzophenone azine by contacting benzophenone in the presence of copper (I) chloride and either of zinc chloride and ammonium chloride with a mixed gas of ammonia and oxygen at atmospheric pressure is disclosed in *Chemistry Letters*, 1974, pp. 89–90 and 1097–1098, by Hiromu Hayashi et al, or under increased pressure is disclosed in *Industrial Engineering Chemistry, Product Research and Development*, Vol. 15, No. 4, 229 – 303 (1976), by Hiromu Hayashi et al.

In these processes, the reaction is carried out in a homogeneous liquid-phase system so that complicated processes are required for the separation, recovery and circulation of the expensive catalyst. This causes various problems, for example, an increase in equipment cost or energy cost and the use of special solvents, which become difficulties from an industrial standpoint.

An explanation of these difficulties in the prior art is given in more detail below with reference to a typical example, the production of benzophenone azine.

The formation of benzophenone azine from diphenylmethane imine is shown by the following equation (1).

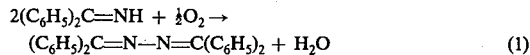

The formed benzophenone azine produces hydrazine and benzophenone according to equation (2) and the benzophenone can be used for the production of diphenylmethane imine by reaction with ammonia according to equation (3), and the resulting imine can be used repeatedly as a material for reaction (1).

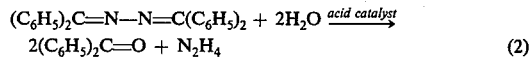

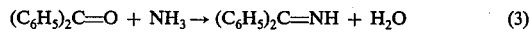

Further in the prior art, copper (I) chloride is used as a catalyst in reaction (1). *Nippon Kagaku Kaishi*, 1973, pp. 1949–1953 discloses that copper (I) chloride and diphenylmethane imine form a 1:1 complex, $CuCl\cdot(C_6H_5)_2C=NH$, and that this complex is converted to benzophenone azine through an oxygen containing copper (II)-imine complex which results from the above 1:1 complex by the absorption of a quarter of a mole of oxygen. Further, *Nippon Kagaku Kaishi*, 1975, pp. 242–245 discloses that a temperature higher than 120° C should be applied for the formation of benzophenone azine by dehydrogenation of diphenylmethane imine which is a ligand of the oxygen containing copper (II)-imine complex. Still further, it is well known that benzophenone azine can be obtained even at room temperature when pyridine is used as a solvent (as disclosed in U.S. Pat. No. 2,870,206), and this means that the reaction temperature of reaction (1) can be decreased to a large extent. However, when reaction (1) is carried out in a pyridine solvent, various difficulties are encountered. For example, the separation of the catalyst becomes extremely difficult, and, in addition, contamination of the material for reaction (1) with benzophenone cannot be avoided, since benzophenone and diphenylmethane imine have boiling points very close to each other. Accordingly, benzophenone accumulates in the pyridine, which makes a continuous production of the azine impossible.

SUMMARY OF THE INVENTION

Extensive studies have now been made to overcome these drawbacks of the prior art and a method for the production of benzophenone azine which comprises fixing the catalyst on a specially devised resin in the form of a coordination polymer complex and passing liquid diphenylmethane imine as a starting material through a layer of the resin, or blowing molecular oxygen into liquid diphenylmethane imine with the fixed catalyst suspended therein, whereby separation of the catalyst becomes unnecessary or is extremely simplified, has now been developed.

Accordingly, the present invention in one embodiment provides a high molecular weight catalyst for the production of ketazines, comprising a copper (I) halide or a methoxy copper (II) halide coordinated to a synthetic resin containing therein monodentate pyridine groups as functional groups, and also, in another embodiment, provides a method for producing a ketazine, which comprises contacting a ketimine with molecular oxygen in the presence of the high molecular weight catalyst described above.

DETAILED DESCRIPTION OF THE INVENTION

In the present invention, examples of synthetic resins containing therein monodentate pyridine groups as functional groups include poly(4-vinylpyridine), poly(2-vinylpyridine) and a copolymer of divinylbenzene and at least one of 2-vinylpyridine and 4-vinylpyridine. Various copolymers of these monomers can be employed and the copolymers which are suitable can have differing N values as defined hereinafter, specific surface areas and structures, depending on the divinylbenzene content and polymerization media.

Examples of suitable copper (I) halides which can be used include copper (I) chloride and copper (I) bromide.

Coordination of the copper (I) halide to the resin is carried out by suspending the resin, preferably in the presence of oxygen, in a copper (I) halide solution or suspension which may contain as a third component at least one member selected from the group consisting of vinylpyridine monomer, low molecular weight vinylpyridine polymer and diphenylmethane imine, followed by filtration and drying. Examples of liquid media which can be used in the reaction include ethanol and chloroform.

Suitable examples of methoxy copper (II) halides which can be employed include methoxy copper (II) chloride, $CuOCH_3Cl$, and methoxy copper (II) bromide, $CuOCH_3Br$. The methoxy copper (II) halides can easily be prepared by the reaction between a copper (I) halide and oxygen in an excess amount of methanol at room temperature (about 20° – 30° C) for 1 to 2 hours in accordance with reaction (4).

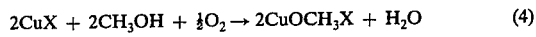
$$2CuX + 2CH_3OH + \tfrac{1}{2}O_2 \rightarrow 2CuOCH_3X + H_2O \qquad (4)$$

wherein X is a halogen such as chlorine or bromine. The resulting reaction product containing the methoxy copper (II) halide may be subjected to the subsequent coordination as it is, or the methoxy copper (II) halide separated from the reaction product by filtration may be subjected thereto.

The coordination can be effected by suspending the above-described resin and the methoxy copper (II) halide in methanol.

Alternatively, the present catalyst comprising the methoxy copper (II) halide can be prepared directly by mixing a copper (I) halide with a suspension of the above-described resin in methanol and then introducing oxygen thereinto, whereby the coordination reaches the degree, Cu/N = 1, wherein N is the number of pyridine groups contained in the resin, i.e., the number of equivalents of hydrochloric acid consumed in an acid-base titration.

As the material for producing benzophenone azine, diphenylmethane imine can be used alone or in admixture with benzophenone. Use of the mixture is very advantageous from the following standpoints: (i) in reaction (3), a mixture of diphenylmethane imine and benzophenone is produced by reacting ammonia with an excess of benzophenone, and this mixture can be used as it is, and (ii) the reaction temperature at which benzophenone azine is produced may be selected optionally over a wide temperature range of room temperature to about 200° C. The melting point of benzophenone and benzophenone azine is 48° and 164° C, respectively, and diphenylmethane imine is a liquid at room temperature. Accordingly, an advantageous reaction temperature is 164° C or higher when the benzophenone imine is reacted in the absence of benzophenone, whereas a temperature of 164° C or higher is not advantageous from the standpoint of stability of the present high molecular weight catalyst. The reaction can be effectively carried out at a temperature of about 80° to about 160° C, particularly preferably at about 120° to about 135° C, when a benzophenone mixture comprising about 20 to about 50% by weight of diphenylmethane imine is used.

The catalyst of the present invention may be used in the form of a suspension in the reaction system, and the separation of catalyst is easily carried out using a conventional mechanical solid-liquid separation operation such as deposition, filtration and centrifugation, and conventional chemical treatments such as dissolution, extraction and regeneration are not necessary.

The present invention will be illustrated in greater detail with reference to the following examples, which are not, however, to be interpreted as limiting the invention thereto. Unless otherwise indicated herein, all parts, percentages, ratios and the like are by weight.

EXAMPLE 1

Under a nitrogen atmosphere, a monomer mixture of 4-vinylpyridine and divinylbenzene in a weight ratio of 55:45, and a polymerization initiator, AIBN (2,2'-azobisisobutyronitrile) ($2 \times 10^{-3}$ mole/l) were mixed with 10 times by volume of methanol, and the reaction was effected at 70° C for 16 hours. The conversion of monomer was 85%. The resulting agar-like swelled gel was cut finely, spread on a porcelain plate and air-dried. The dried gel was refluxed in methanol for 1 hour, and the mixture was then subjected to decantation. The supernatant liquid was separated to remove the remaining monomer. The residue obtained was air-dried, and then dried in vacuo at 120° C. Thus, a copolymer of 4-vinylpyridine and divinylbenzene (N = 3.75 meq/g) was obtained.

Into a suspension of 3.0 g of the copolymer in 50 ml of methanol was added 1.11 g of copper (I) chloride, and the mixture was stirred for 2 hours under an oxygen atmosphere, whereby the resin became a deep green color. The reaction mixture was allowed to stand overnight, and then filtered to collect a product, which was dried. Thus, a catalyst comprising methoxy copper (II) chloride (Cu/N = 0.925) was obtained.

The thus obtained catalyst (0.29 g, 0.73 g and 1.45 g each which corresponds to 0.2 g, 0.5 g and 1.0 g of the resin, respectively) was mixed with 18.2 g of a benzophenone comprising 35% by weight of diphenylmethane imine, and oxygen was introduced thereinto at 120° C for 1 hour at 2 l/hr, while the mixture was stirred. The yield of benzophenone azine was 61, 86 and 92%, respectively.

EXAMPLE 2

The procedures for the preparation of the catalyst described in Example 1 were repeated, except that a monomer mixture of 4-vinylpyridine and divinylbenzene in a weight ratio of 60:40 was used, whereby a catalyst comprising methoxy copper (II) chloride was obtained (N = 3.81 meq/g, Cu/N = 0.913).

The resulting catalyst (0.29 g, 0.73 g and 1.45 g each) was mixed with 18.2 g of a benzophenone comprising 35% by weight of diphenylmethane imine, and oxygen was introduced thereinto at 120° C for 1 hour at 2 l/hr, while the mixture was stirred. The yield of benzophenone azine was 50, 88 and 86%, respectively.

EXAMPLE 3

The procedures for the preparation of the catalyst described in Example 1 were repeated, except that a monomer mixture of 4-vinylpyridine and divinylpyridine in a weight ratio of 80:20 was used, whereby a catalyst comprising methoxy copper (II) chloride was obtained (N = 5.6 meq/g, Cu/N = 0.17).

The resulting catalyst (4.27 g) was mixed with 18.2 g of a benzophenone comprising 35% by weight of diphenylmethane imine, and oxygen was introduced thereinto at 120° C for 3 hours at 2 l/hr, while the mixture was stirred. The yield of benzophenone azine was 93%.

The used catalyst was recovered and reused for the production of benzophenone azine under the same conditions described above. The yield thereof on the 2nd and 3rd reuse was 89 and 86%, respectively.

EXAMPLE 4

With a suspension of 10.0 g of poly(4-vinylpyridine) (Sumichelate CR-2; N = 4.66 meq/g, a product of Sumitomo Chemical Company, Limited) in 110 ml of methanol, was mixed 1.05 g of copper (I) chloride, and then oxygen was introduced thereinto overnight, while the mixture was stirred. Thus, a catalyst comprising methoxy copper (II) chloride was obtained in an amount of 12.11 g (Cu/N = 0.20).

The thus obtained catalyst (4.61 g) was mixed with 18.2 g of a benzophenone comprising 35% by weight of diphenylmethane imine, and oxygen was introduced thereinto at 120° C for 3 hours at 2 l/hr, while the mixture was stirred. The yield of benzophenone azine was 59%.

EXAMPLE 5

The procedures for the preparation of the copolymer described in Example 1 were repeated, except that toluene was used as the polymerization medium in place of methanol. The resulting copolymer was refluxed in methanol for 1 hour, air-dried and then dried in vacuo.

3 g of the resulting methanol insoluble copolymer (N = 3.34 meq/g) was mixed with 50 ml of methanol and 0.994 g of copper (I) chloride, and then oxygen was introduced to the mixture in a manner similar to that of Example 1. Thus, a catalyst comprising methoxy copper (II) chloride was obtained (Cu/N = 0.904).

The resulting catalyst (0.72 g) was mixed with 18.2 g of a benzophenone comprising 35% by weight of diphenylmethane imine, and then oxygen was introduced thereinto at 120° C for 1 hour at 2 l/hr, while the mixture was stirred. The yield of benzophenone azine was 46%.

EXAMPLE 6

The procedures for the preparation of the copolymer described in Example 1 were repeated, except that an aqueous medium comprising 0.17% by weight of water soluble polyvinyl alcohol ($\bar{P}n$ = 500) was used in place of methanol and copolymerization was effected at 90° C for 4 hours. The resulting copolymer was refluxed for 1 hour in methanol.

3 g of the resulting copolymer (N = 3.96 meq/g) was mixed with 50 ml of methanol and 1.18 g of copper (I) chloride to obtain a catalyst comprising methoxy copper (II) chloride (Cu/N = 0.939).

The catalyst (0.73 g) was mixed with 18.2 g of a benzophenone mixture comprising 35% by weight of diphenylmethane imine, and then oxygen was introduced thereinto at 120° C for 1 hour at 2 l/hr, while the mixture was stirred. The yield of benzophenone azine was 67%.

EXAMPLE 7

The procedures of Example 1 were repeated, except that the introduction of oxygen was effected at 100°, 135° and 160° C using 0.29 g of the catalyst, to obtain the azine in yields of 20, 89 and 89%, respectively.

EXAMPLE 8

1.5 g of copper (I) chloride and 4.7 g of poly(4-vinylpyridine) resin (Sumichelate CR-2, produced by Sumitomo Chemical Co., Ltd.) were added to 50 ml of ethanol. The mixture was stirred for 4 hours in the presence of oxygen to obtain a catalyst containing CuCl of 0.079 g/g of dry resin. Thereafter, 4.1 g (CuCl 0.3 g) of this catalyst was added to 18.2 g of a benzophenone mixture comprising 35% by weight of diphenylmethane imine, and then oxygen was passed through the mixture at 120° C under atmospheric pressure. Thus, 104 ml of oxygen was absorbed in 3 hours to obtain 1.7 g of benzophenone azine (yield 27%).

EXAMPLE 9

5.2 g of diphenylmethane imine and 1.5 g of copper (I) chloride were added to 100 ml of chloroform and the mixture was stirred in the presence of oxygen. After the precipitate was filtered off, 10.0 g of poly(4-vinylpyridine) resin (Sumichelate CR-2) was added to the resulting black green filtrate, and the mixture was allowed to stand overnight. Thus, the copper formed a linkage with the resin whereby the color of the solution changed to yellow. By filtration and drying, a catalyst containing CuCl of 0.10 g/g of dry resin was obtained. Thereafter, 4.52 g (CuCl 0.38 g) of this catalyst was added to 18.2 g of a benzophenone mixture comprising 35% by weight of diphenylmethane imine, and then oxygen was passed through the mixture, at 120° C under atmospheric pressure, at a rate of 2 l/hr. Thus, 5.2 g of benzophenone azine (yield 81%) was obtained in 3 hours.

EXAMPLE 10

2.6 g of diphenylmethane imine and 0.75 g of copper (I) chloride were added to 50 ml of chloroform and the mixture was stirred in the presence of oxygen. After the precipitate was filtered off, 6.1 g of a 4:6 weight ratio copolymer resin of divinylbenzene and 2-vinylpyridine was added to the resulting black green filtrate, and the mixture was allowed to stand overnight. Thus, a catalyst containing CuCl of 0.019 g/g of dry resin was obtained. Thereafter, 4.85 g (CuCl 0.09 g) of this catalyst was added to 18.2 g of a benzophenone mixture comprising 35% by weight of diphenylmethane imine, and then oxygen was passed therethrough, at 120° C under atmospheric pressure, at a rate of 2 l/hr. Thus, 2.9 g of benzophenone azine (yield 45%) was obtained in 3 hours.

While the invention has been described in detail and with reference to specific embodiments thereof, it will be apparent to one skilled in the art that various changes and modifications can be made therein without departing from the spirit and scope thereof.

What is claimed is:

1. A method for producing a ketazine by contacting a ketimine with molecular oxygen in the presence of a catalyst comprising a high molecular weight resin in which a copper (I) halide or a methoxy copper (II) halide is coordinated to a synthetic resin containing therein monodentate pyridine groups as functional groups, wherein the synthetic resin is poly(4-vinylpyridine), poly(2-vinylpyridine) or a copolymer of divinylbenzene and at least one member selected from the group consisting of 2-vinylpyridine and 4-vinylpyridine.

2. The method according to claim 1, wherein the copper (I) halide is copper (I) chloride or copper (I) bromide.

3. The method according to claim 1, wherein the methoxy copper (II) halide is methoxy copper (II) chloride ($CuOCH_3Cl$) or methoxy copper (II) bromide ($CuOCH_3Br$).

4. The method according to claim 1, wherein the coordination degree, Cu/N, of said catalyst is up to 1, wherein N is the number of pyridine groups present in the synthetic resin.

5. The method according to claim 1, wherein said catalyst comprises further a third component selected from the group consisting of vinylpyridine monomer, low molecular weight vinylpyridine polymer and diphenylmethane imine.

* * * * *